United States Patent [19]

Luccarelli

[11] Patent Number: 5,212,871
[45] Date of Patent: May 25, 1993

[54] MEASURING DEVICE FOR AN ORTHODONTIC BAND

[76] Inventor: Steven J. Luccarelli, 953 Highland Ave., Pelham Manor, N.Y. 10803

[21] Appl. No.: 890,657

[22] Filed: May 28, 1992

[51] Int. Cl.$^5$ ............... G01B 3/10; G01B 5/08; A61B 5/107; A61C 19/04
[52] U.S. Cl. ................... 33/555.4; 33/514; 128/777
[58] Field of Search ......... 33/555.4, 511, 512, 33/513, 514, 514.1, 555.1, 555.2, 732, 755, 756, 759; 128/777, 776

[56] References Cited

U.S. PATENT DOCUMENTS

| 855,875 | 6/1907 | Bode | 33/514 |
|---|---|---|---|
| 984,040 | 2/1911 | Siverling | 33/514 |
| 1,036,927 | 8/1912 | Struble, Jr. | 33/514 |
| 1,233,131 | 7/1917 | Schwartz | 33/514 |
| 1,772,352 | 8/1930 | Huber | 33/555.4 |
| 3,839,801 | 10/1974 | Tappe | 33/514 |
| 3,889,382 | 6/1975 | Husted et al. | 33/514 |
| 4,791,940 | 12/1988 | Hirschfeld et al. | 128/777 |

FOREIGN PATENT DOCUMENTS

| 462548 | 6/1928 | Fed. Rep. of Germany | 33/555.4 |
|---|---|---|---|
| 596208 | 4/1934 | Fed. Rep. of Germany | 33/514 |
| 762856 | 4/1934 | France | 33/514 |
| 1131971 | 3/1957 | France | 33/555.4 |

OTHER PUBLICATIONS

Copy of operating manual for "Dentometer" manufactured by FROL Corp., Grass Valley, California.
Brochure from FROL Corporation for "The Dentometer".

Primary Examiner—Thomas B. Will
Assistant Examiner—C. W. Fulton
Attorney, Agent, or Firm—Collard & Roe

[57] ABSTRACT

A device for measuring the circumference of a tooth or other object, having a longitudinally extending handle with a first end, a second end, an exterior and a hollow interior. A rotatably mounted head portion is disposed at the first end of the handle, and has an aperture which connects the hollow interior to the exterior of the handle. The head portion is adjustable to locate the aperture at a particular angle with respect to the longitudinal axis of the handle. A band is provided which has two ends and a central portion. The central portion is located exteriorly of the handle and forms a loop to be placed around the tooth or other object. The ends pass through the aperture of the head portion into the hollow interior. A tightening lever is pivotally connected to the handle and the ends of the band for retracting the band through the aperture into the hollow interior, to tighten the loop around the tooth or other object to be measured. A display is mounted on the exterior of the handle and coupled to the tightening lever for indicating the circumference of the tooth or other object to be measured.

13 Claims, 4 Drawing Sheets

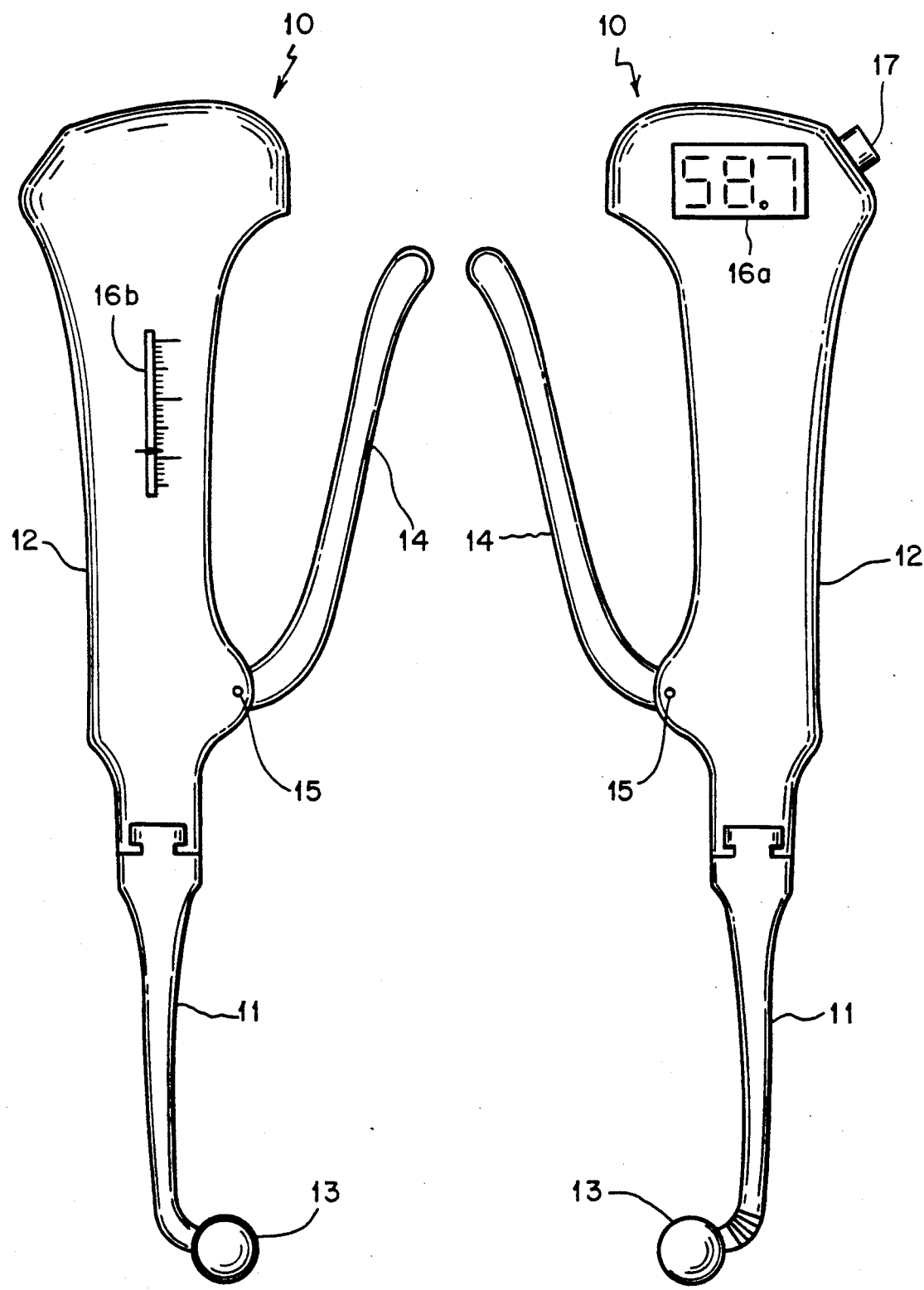

MEASURING DEVICE FOR AN ORTHODONTIC BAND

BACKGROUND OF THE INVENTION

1. Field of the Invention

The present invention relates to a device which measures the circumference of a tooth in order to properly fit an orthodontic band. More specifically, the measuring device has a loop which is placed around the tooth to be measured in order to determine its circumference.

2. The Prior Art

In the practice of orthodontics, there are two basic types of attachments, bands and brackets. A band is a thin strip of stainless steel which is placed around the circumference of a tooth and cemented in place. An orthodontic bracket is then welded to the band. The band is used solely to hold the orthodontic bracket onto the tooth. A bracket may also be bonded or glued directly to the surface of the tooth.

Bands are manufactured in various sizes with attachments already welded to the band. When the appropriate size band is chosen, it is then fitted and adapted to the individual morphology of that tooth. Previously, it was difficult to select the appropriate size band for a given tooth. The dentist would typically examine a tooth and simply guess at what size band would fit. If a band was the incorrect size, the orthodontist would select a larger or smaller band until he found the proper size. The bands which were tested but were the incorrect size would then have to be sterilized and resorted.

One appliance that has been used in the past for measuring the diameter of a tooth is the Dentometer manufactured by the Frol Corporation. This appliance is designed to measure anterior and some posterior teeth by placing the Dentometer perpendicular to the tooth surface and placing the measuring loop around the tooth. A measurement is then taken by using two fingers to rotate the take u knob which eliminates slack in the measuring loop. The take up knob is connected to a needle on a dial which will then indicate a number on a slip cover on the dial. Once the loop is snug around the tooth the operator will then read the dial and look up this number on the information guide to find the band size. When the Dentometer is used to measure posterior teeth, the cheek must be retracted in order to have access to the first and second molars. This makes it very difficult to measure posterior teeth, especially teeth which are farther back in the mouth, i.e., second molars are more difficult to measure than first molars. The Dentometer has not been recommended for use in measuring third molars.

The Dentometer is designed to measure teeth with the patient in a seated or a near vertical position. The Dentometer instructs the operator to hold the instrument with the palm facing down with the thumb and index finger pointing toward the mouth. The thumb and index finger are needed to adjust the knob, leaving three fingers to hold the appliance. Because the Dentometer has a needle with a removable slip cover, the angle at which the measurement is read can effect the accuracy of the reading.

SUMMARY OF THE INVENTION

It is therefore an object of the present invention to overcome the drawbacks of the prior art and to provide a measuring device which can quickly and accurately measure all teeth.

It is a further object of the present invention to provide a measuring device with a separable head which can be autoclaved.

It is still a further object of the present invention to provide a measuring device which provides an accurate reading from any angle.

These and other related objects are achieved by a measuring device having a measuring loop which is used to measure the circumference of a tooth. Before each use, the loop is placed around a cylinder of a known size in order to calibrate the measuring device. Once calibrated, the measuring loop is then placed around the tooth to be measured with the handle of the measuring device extending at a convenient angle from the tooth surface. The measuring loop is slowly tightened until it is snug around the tooth. The display will then indicate the circumference of the tooth so that an appropriate sized band may be selected.

When the measuring device is used, the orthodontist is seated and the patient is reclined. The measuring device is held in the orthodontist's hand with his palm facing upward or toward the head of the patient. The handle portion of the measuring device containing the read out can be rotated so that the measurement can be seen regardless of the tooth angle.

The device for measuring the circumference of a tooth or other object includes a longitudinally extending handle, having a first end, a second end, an exterior and a hollow interior. A rotatably mounted head portion is disposed at the first end of the handle and has an aperture for connecting the hollow interior to the exterior of the handle. The head portion is adjustable to locate the aperture at a particular angle with respect to the longitudinal axis of the handle. A band is provided which has two ends and a central portion. The central portion is located exteriorly of the handle and forms a loop to be placed around the tooth or other object. The ends of the band pass through the aperture of the head portion into the hollow interior, with one end attached to the handle. Tightening means are operatively connected to the handle and the other end of the band for retracting the end of the band through the aperture into the hollow interior to tighten the loop around the tooth or other object to be measured. Display means are mounted on the exterior of the handle and are coupled to the tightening means for indicating the circumference of the tooth or other objects to be measured.

The device may additionally include tension control means for limiting the amount of tension exerted on the tooth by the tightening means without interfering with the measurement. Calibration means are provided for calibrating the display means, by tightening the loop around the cylinder of known circumference and adjusting the display means to show the known circumference.

The head portion and the band are removable for sterilization. Alternately the head and band may be disposable. The head portion is adjustable to locate the aperture in the range of 0° to 180° with respect to the longitudinal axis of the handle. The range is preferably 45° to 90°, with the aperture being adjustable throughout the range. The aperture may be off-set 45° or 90° without being adjustable.

The tightening means includes a lever pivotally mounted on the handle, having an end located within the hollow interior and attached to the other end of the band. Pivotal movement of the lever retracts the end of the band into the hollow interior, to tighten the loop around the tooth. The display means includes two LED displays mounted on opposite sides of the handle.

In an alternate embodiment, the device for measuring the circumference of a tooth or other object includes a longitudinal extending handle, having a first and a second end, an exterior and a hollow interior. A rotatably mounted head portion is disposed at the first end of the handle and has an aperture for connecting the hollow interior to the exterior of the handle. The head portion is adjustable to locate the aperture at a particular angle with respect to the longitudinal axis of the handle. A band is provided, which has two ends and a central portion. The central portion is located exteriorly of the handle and forms a loop to be placed around the tooth or other object. The ends pass through the aperture into the hollow interior. Tightening means are operatively connected to the handle and to the ends of the band for retracting the ends through the aperture into the hollow interior to tighten the loop around the tooth or other object to be measured. Display means are mounted on the exterior of the handle and are coupled to the tightening means for indicating the circumference of the tooth or other object to be measured.

The device may also include tension control means for limiting the amount of tension exerted on the tooth by the tightening means without interfering with the measurement. Also calibration means may be provided for calibrating the display means by tightening the loop around the cylinder of known circumference and then adjusting the display means to show the known circumference.

The head portion and band may be removable from the handle for sterilization or disposal after each use. The head portion is adjustable to locate the aperture in the range of 0° to 180° with respect to the longitudinal axis of the handle. The aperture is preferably adjustable in the range of 45° to 90°. The aperture may also be fixed at 45° or 90°.

The display means may include a scale mounted on opposite exterior sides of the handle. The tightening means may include a pivotally mounted lever and an indicator. The handle may be provided with a slot adjacent to the scale, with the indicator exiting therefrom. The position of the indicator with respect to the scale corresponds to the circumference of the tooth. The tightening means may also include a take-up reel which retracts the loop by means of gears or pulleys.

BRIEF DESCRIPTION OF THE DRAWINGS

Other objects and features of the present invention will become apparent from the following detailed description considered in connection with the accompanying drawings which disclose several embodiments of the present invention. It should be understood, however, that the drawings are designed for the purpose of illustration only and not as a definition of the limits of the invention.

In the drawings, wherein similar reference characters denote similar elements throughout the several views:

FIG. 1 is a top plan view of the measuring device according to the invention;

FIG. 2 is a bottom view of an alternate embodiment of the measuring device;

DETAILED DESCRIPTION OF PREFERRED EMBODIMENTS

Figure 3:
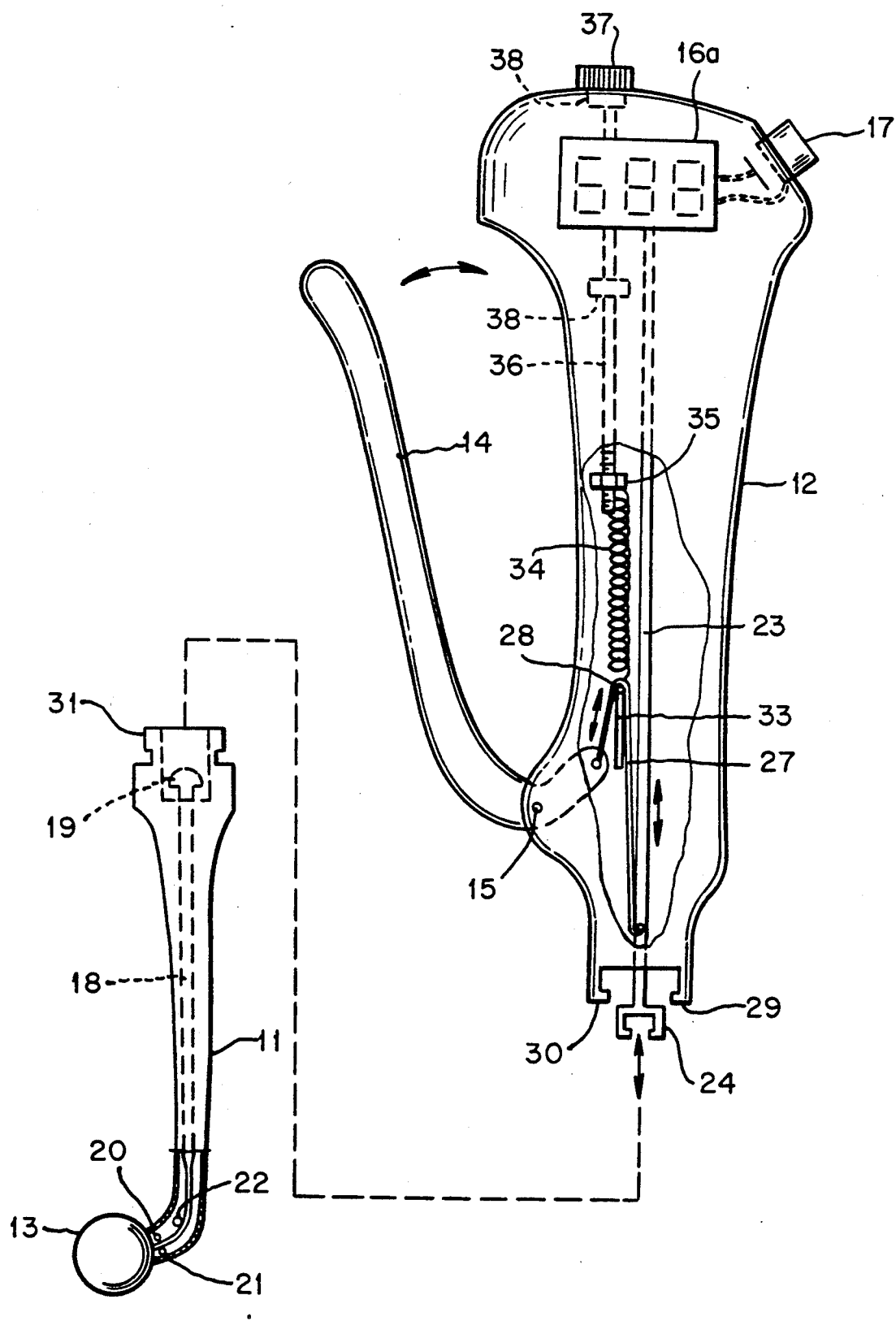
FIG. 3 is an exploded view in partial cross section of the measuring device according to FIG. 1.

Turning now in detail to the drawings and, in particular, FIG. 1, there is shown a measuring device 10 having a head 11 and a handle or shaft 12. Head 11 has a measuring loop 13 at one end flexibly mounted to make it easier to place it over the tooth to be measured. Handle 12 includes a lever 14 which is pivotally attached to handle 12 at pivot point 15. FIG. 1 shows a calibration button 17 which is located on the end of handle 12 in the vicinity of a display 16a. Display 16a is a digital display, while display 16b, as shown in FIG. 2, is an analog display. Whichever display type is utilized, two displays can be provided on opposite sides of handle 12.

As shown in FIG. 3, head portion 11 includes a longitudinally-extending internal rod 18. Rod 18 has a knob 19 located at one end and measuring loop 13 connected to the other end. Measuring loop 13 passes through a narrow opening in the end of head 11 formed by pins 20 and 21, and then passes around axle 22 before being connected to rod 18. One or both ends of measuring loop 13 may be connected to rod 18. If only one end is connected, the other end may be attached to the end of head 11, or one of the pins.

Figure 4:
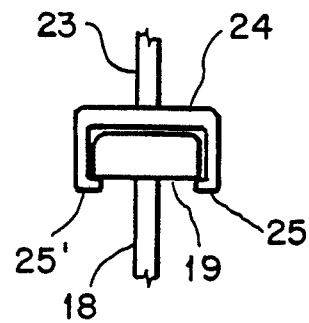
FIG. 4 is a cross-sectional view of the connection between the head and handle of the measuring device.
Figure 5:
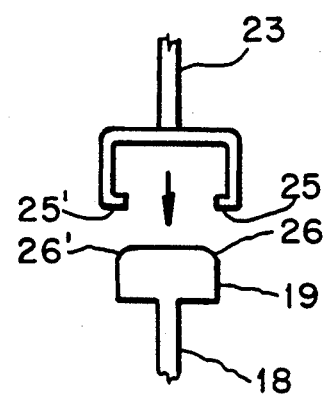
FIG. 5 shows the head and handle disengaged.

Handle 12 contains a second internal rod 23. One end of rod 23 is formed as a U-shaped clip 24 having inwardly-facing abutments 25 to securely engage knob 19, as seen in FIGS. 4 and 5. To insert knob 19 into U-shaped clip 24, head 11 is brought into alignment with handle 12 and press-fitted or snapped together so that head 11 and handle 12 form a non-flexible outer casing. Knob 19, which has rounded edges 26, presses abutments 25 apart so that knob 19 can be fully received within U-shaped clip 24. Rods 18 and 23 can now move along the longitudinal direction as a single unit. Handle 12 has a U-shaped clip 29 with abutments 30 for releasably engaging the end 31 of head 11. The measuring device may also be manufactured as a single piece, i.e. head and handle are one piece. The measuring device may also include a swivel connection between head 11 and handle 12, so that handle 12 can be rotated to allow simpler viewing of the display.

As seen in FIG. 3, when lever 14 is pivoted about pivot point 15 towards handle 12, a cable 27 connected to lever 14 slides around pulley 28, pulling the rods 18 and 23 towards display 16a. As rod 23 moves towards display 16a, the amount that rod 23 has moved is electronically registered and shown on display 16a, as shown in FIG. 1, or shown directly on the scale of display 16b.

The mechanism which is used to tighten measuring loop 13 may be equipped with a tension control mechanism which limits the amount of tension that can be exerted by measuring loop 13 on the tooth. Once measuring loop 13 is sufficiently tightened around the patient's tooth to obtain an accurate measurement, further pressure on lever 14 will have no effect on the tension of measuring loop 13. For example, the axle of pulley 28, as seen in FIG. 3, may be slidably mounted within a channel 33. Pulley 28 may be movable in a direction parallel to rod 23 and may be equipped with a spring 34 having a predetermined tension which biases pulley 28 towards display 16a. Once the tension value of measuring loop 13 is sufficient to obtain an accurate measurement, further pressure on lever 14 will move pulley 28 along channel 33 against the biasing force of spring 34. Movement of pulley 28 will not effect the movement of rod 23 or the measurement of the circumference of the tooth.

Spring 34 is connected between the axle of pulley 28 and nut 35. Nut 35 is mounted on a bolt 36, which has an end knob 37. Bolt 36 is held in place by blocks 38. One or more blocks may be provided depending on the tension values required. Rotation of end knob 37 causes nut 35 to ride along bolt 36, increasing or decreasing the tension o spring 34 and pulley 28. Blocks 38 prevent vertical movement of bolt 36, while freely allowing rotation. Spring 34 is designed to be several times longer than channel 33, i.e. the maximum length that pulley 28 may travel. The spring should therefore be long enough so that its linear characteristics are maintained no matter what tension value is chosen.

Figure 6:
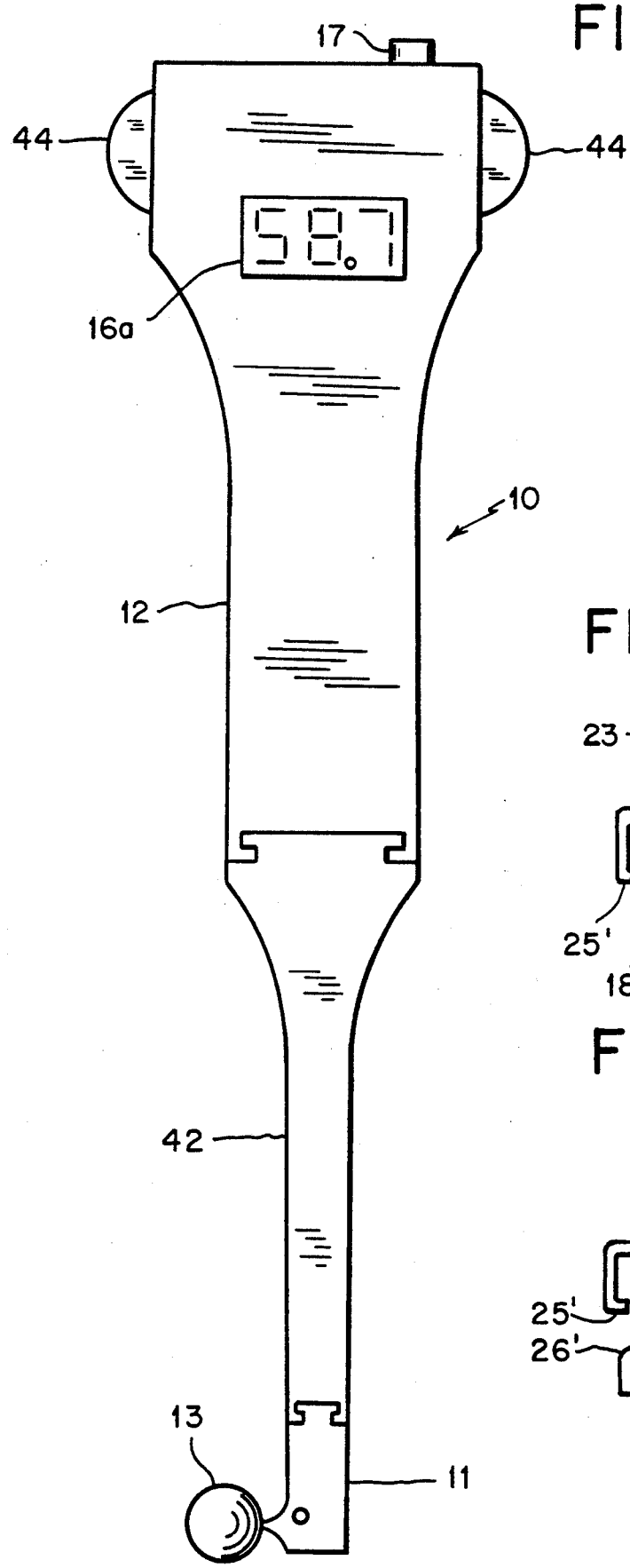
FIG. 6 is a top plan view of an alternate embodiment of the measuring device.
Figure 7:
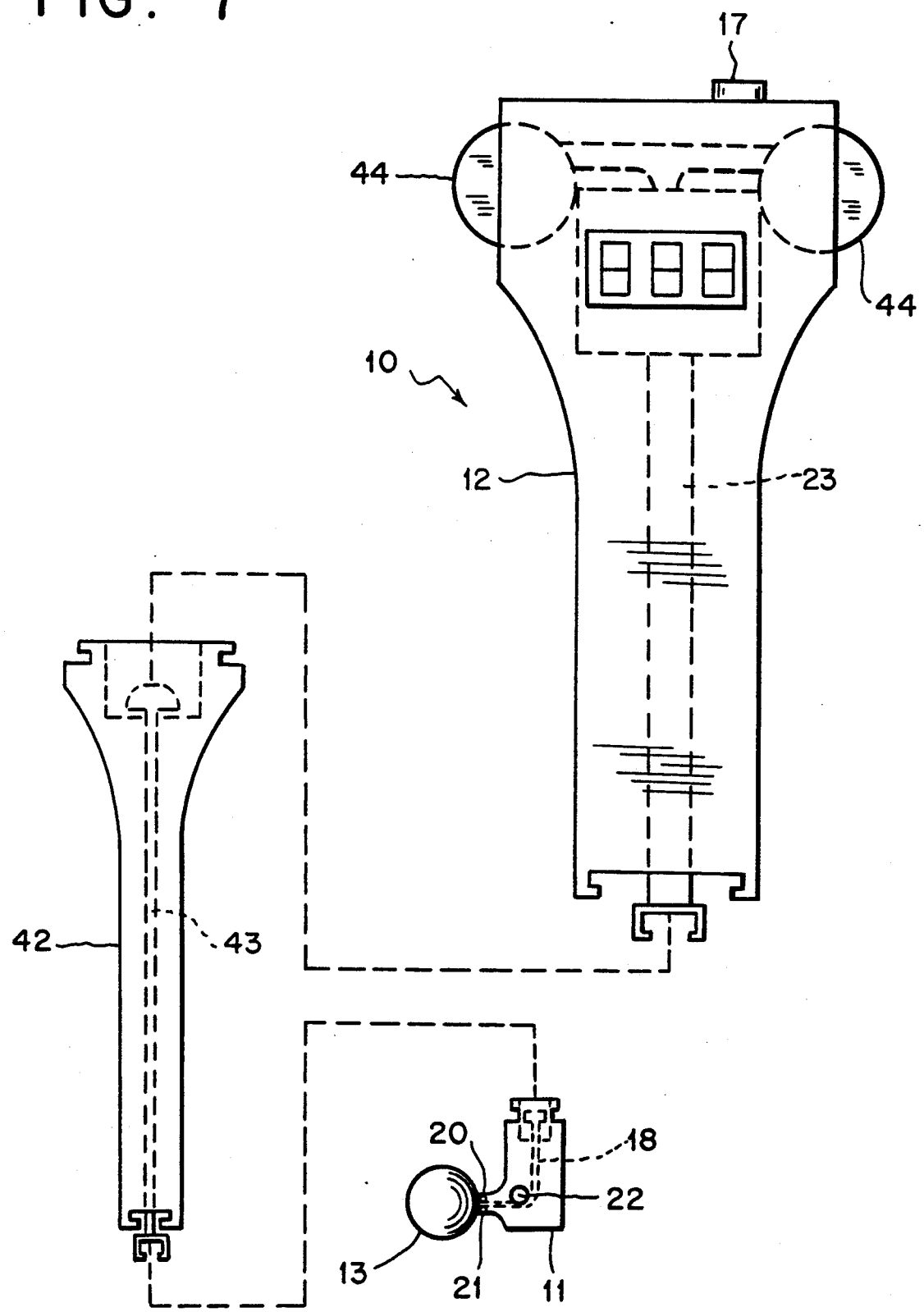
FIG. 7 is an exploded view of the measuring device according to FIG. 6.

An alternate embodiment of measuring device 10 is shown in FIGS. 6 and 7. Components of FIGS. 6 and 7 which correspond to the embodiment of FIGS. 1-5 will be similarly numbered. Measuring device 10 includes a head 11, an extension 42, and a handle 12. Head 11, extension 42 and handle 12 press fit together to form a non-flexible exterior structure. Rod 18, within head 11, engages with an extension rod 43 in a press fit manner. Extension rod 43, in turn, engages with rod 23 in a press fit manner. The rods are moved by rotating a take-up reel 44. As shown in FIG. 3, measuring loop 13 is mounted at a 45° angle. As shown in FIG. 6, measuring loop 13 is mounted at an angle of approximately 90° with respect to the longitudinal axis of head 11, extension 42, and handle 12.

Measuring loop 13 extends from head 11 at an angle similar to that of known dental instruments. The angle can be in the range of 0 to 180°, preferably 45° to 90°. Measuring loop 13 can be fixed or it may be pivotable so that the technician can adjust the angle according to the particular application. Head 18 may be swivelled with respect to extension 42 or handle 12 in order to permit simpler viewing of the display.

The measuring device is calibrated as follows: Measuring loop 13 is placed around a standard size cylinder and lever 14 or take-up reel 44 is activated to retract rod 23, extension rod 43 and rod 18, thus closing measuring loop 13 around the standard size cylinder. Once measuring loop 13 is snug, calibration button 17 is depressed and display 16a, is set to the circumference of the standard cylinder. The measuring device is accurate to 0.010 inches corresponding to the difference in band sizes. As seen in FIG. 3, calibration button makes contact with a calibration circuit within display 16a.

Once calibrated, the measuring device may be used as follows: The individual taking the measurement holds measuring device 10 with their palm facing upwards. Measuring loop 13 is then placed around the tooth to be measured. Lever 14, as shown in FIGS. 1 and 2 is then pivoted towards handle 12 until measuring loop 13 is snug around the tooth to be measured. Alternatively, take-up reel 44 can be activated to retract measuring loop 13, as shown in FIG. 6. The circumference is then read off display 16a or 16b. Once lever 14 is released and measuring loop 13 is removed from the tooth, the next tooth can be measured. In order to facilitate measuring, measuring loop 13 is offset from the longitudinal axis of head 11 and handle 12.

Head 11 and measuring loop 13 must be sterile before each use since it is placed into the patient's mouth. Head 11 and measuring loop 13 can be disposable, for example. A new head assembly could be pre-sterilized and hermetically sealed in plastic. Just prior to use, the individual taking the measurement would remove the head assembly from the plastic container, calibrate the device, measure the patient's teeth, and then dispose of the head assembly. Alternatively, head assembly 11 could be removed from handle 12 and autoclaved prior to each use.

Take up reel 44 may be provided with a clutch mechanism which prevents rod 23 from being retracted, once a predetermined tension value of measuring loop 13 has been obtained. The clutch would allow take-up reel 44 to continue rotating without further retracting rod 23. The clutch may be in the form of a one-way slip clutch, for example, similar to a device found on late model automobile gas tank caps. Although the display 16a is a digital display, e.g., LED display, the display can be of any analog or digital type. For example, the display may consist of a needle which sweeps across a calibrated dial or face plate, as shown in FIG. 2, to correspond to the circumference of the tooth.

While several embodiments of the present invention have been shown and described, it is to be understood that many changes and modifications may be made thereunto without departing from the spirit and scope of the invention as defined in the appended claims.

What is claimed is:

1. A device for measuring the circumference of a tooth or other object, comprising:
    a longitudinally extending handle having a first end, a second end, and a hollow interior;
    a sterile head portion demountably coupled to said first end of said handle and having at its free end an aperture that is offset from the longitudinal axis of said handle;
    a sterile band having two ends slidably disposed within said head portion and a central portion projecting outwardly from the aperture of the head portion for encircling the tooth or other object, said head portion and said band being readily detachable from said handle for sterilization;
    lever operated tightening means pivotally connected to said handle and operatively connected to said ends of said band, said lever being pivoted toward said handle to retract said band through the aperture of the head into the hollow interior so that said loop is tightened around the tooth or other object;
    display means mounted on said handle and coupled to said tightening means for indicating the circumference of the tooth or other object.

2. The device for measuring the circumference of a tooth according to claim 1, additionally including calibration means for calibrating said display means by tightening said loop around a cylinder of known circumference and adjusting said display means to show the known circumference.

3. The device for measuring the circumference of a tooth according to claim 2, wherein said head portion and said band are removable from said handle for autoclaving.

4. The device for measuring the circumference of a tooth according to claim 3, wherein said head portion is adjustable to locate the aperture in the range of 0° to 180° with respect to the longitudinal axis of said handle.

5. The device for measuring the circumference of a tooth according to claim 4, wherein said lever has an end located within the hollow interior attached to said band.

6. A device for measuring the circumference of a tooth according to claim 5, wherein said display means includes two LED displays mounted on opposite sides of said handle.

7. The device for measuring the circumference of a tooth according to claim 2, wherein said head portion and said band are removable from said handle for disposal after use.

8. The device for measuring the circumference of a tooth according to claim 1, wherein the aperture is off-set from the longitudinal axis of said handle by 45°.

9. The device for measuring the circumference of a tooth according to claim 1, wherein the aperture is off-set from the longitudinal axis of said handle by 90°.

10. A device for measuring the circumference of a tooth according to claim 1, wherein said display means includes a scale mounted on opposite exterior sides of said handle, and wherein said tightening means includes an indicator, said handle having a slot adjacent to said scale with said indicator exiting therefrom; the position of said indicator with respect to said scale corresponding to the circumference of the tooth.

11. The device for measuring the circumference of a tooth according to claim 1, wherein said handle and said display means are rotatable with respect to said head portion so that said handle can be pivoted to bring said display means into view while measuring.

12. The device for measuring the circumference of a tooth according to claim 11, additionally including tension control means coupled to said lever operated tightening means and said band for limiting the amount of tension exerted on the tooth or other object by said lever operated tightening means to a predetermined tension value.

13. The device for measuring the circumference of a tooth according to claim 12, wherein said tension control means includes:

a pulley slidably mounted in the hollow interior of said handle;

an adjustable mount;

a spring coupled between said pulley and said adjustable mount for biasing said pulley in a first direction, said spring exerted a force on said pulley equal to said predetermined tension value; wherein said lever operated tightening means including a cable passing around said pulley and coupled to said band, so that said pulley slides in a direction opposite the first direction against the biasing force of said spring, once the tension exerted on the tooth or other object exceeds said predetermined tension value whereby the tension exerted on the tooth or other object is limited.

* * * * *